(12) United States Patent  (10) Patent No.: US 8,855,268 B1
Safai et al.  (45) Date of Patent: Oct. 7, 2014

(54) SYSTEM FOR INSPECTING OBJECTS UNDERWATER

(75) Inventors: Morteza Safai, Seattle, WA (US); Dallas Steven Scholes, Buckley, WA (US)

(73) Assignee: The Boeing Company, Chicago, IL (US)

( * ) Notice: Subject to any disclaimer, the term of this patent is extended or adjusted under 35 U.S.C. 154(b) by 383 days.

(21) Appl. No.: 13/286,795

(22) Filed: Nov. 1, 2011

(51) Int. Cl.
*G01N 23/203* (2006.01)
*H01J 35/10* (2006.01)

(52) U.S. Cl.
CPC ....... *G01N 23/203* (2013.01); *G01J 2235/1262* (2013.01)
USPC ............. 378/87; 378/130; 378/196; 378/197; 378/198; 378/200

(58) Field of Classification Search
CPC .......... G01N 23/203; H01J 2235/1262; A61B 6/4488
USPC ............. 378/44–50, 57–60, 86–90, 130, 199, 378/200, 196–198
See application file for complete search history.

(56) References Cited

U.S. PATENT DOCUMENTS

| | | | | |
|---|---|---|---|---|
| 1,192,706 | A | | 7/1916 | Thomson |
| 3,532,881 | A | * | 10/1970 | Dewan ........................... 250/255 |
| 3,858,037 | A | * | 12/1974 | Moore et al. ...................... 702/8 |
| 4,734,927 | A | * | 3/1988 | Leguen et al. ................ 378/200 |
| 4,780,901 | A | * | 10/1988 | Gabbay et al. ................ 378/141 |
| 5,237,598 | A | | 8/1993 | Albert |
| 5,326,970 | A | * | 7/1994 | Bayless ...................... 250/269.1 |
| 5,736,636 | A | * | 4/1998 | Mozelev et al. ........... 73/152.05 |
| 5,764,683 | A | | 6/1998 | Swift et al. |
| 5,910,654 | A | * | 6/1999 | Becker et al. .............. 250/269.3 |
| 5,947,051 | A | | 9/1999 | Geiger |
| 6,151,381 | A | * | 11/2000 | Grodzins et al. ................ 378/90 |
| 6,192,104 | B1 | * | 2/2001 | Adams et al. .................... 378/90 |
| 6,249,567 | B1 | * | 6/2001 | Rothschild et al. ............. 378/88 |
| 6,317,387 | B1 | | 11/2001 | D'Amaddio et al. |
| 6,339,635 | B1 | | 1/2002 | Schardt et al. |
| 6,396,901 | B1 | | 5/2002 | Hell et al. |
| 6,442,233 | B1 | * | 8/2002 | Grodzins et al. ................ 378/57 |
| 6,453,007 | B2 | * | 9/2002 | Adams et al. .................... 378/90 |
| 6,459,761 | B1 | * | 10/2002 | Grodzins et al. ................ 378/57 |
| 6,459,764 | B1 | * | 10/2002 | Chalmers et al. ............... 378/88 |

(Continued)

FOREIGN PATENT DOCUMENTS

| | | |
|---|---|---|
| EP | 2275839 A2 | 1/2011 |
| GB | 2212975 A | 8/1989 |
| WO | WO2011008345 A2 | 1/2011 |

OTHER PUBLICATIONS

Extended European Search Report, dated Jul. 30, 2013, regarding Application No. EP12172727.5, 12 pages.

(Continued)

*Primary Examiner* — Allen C. Ho
(74) *Attorney, Agent, or Firm* — Yee & Associates, P.C.

(57) ABSTRACT

A method and apparatus for operating an inspection system is provided. A housing with an x-ray system located inside of the housing is moved in an environment with water relative to a location on a surface of an object to be inspected. The location on the surface of the object is submerged in the water in the environment. A number of components for the x-ray system are cooled using the water around the housing.

18 Claims, 6 Drawing Sheets

(56) References Cited

U.S. PATENT DOCUMENTS

| | | | |
|---|---|---|---|
| 6,621,888 B2 * | 9/2003 | Grodzins et al. | 378/57 |
| 6,658,087 B2 * | 12/2003 | Chalmers et al. | 378/86 |
| 7,010,094 B2 | 3/2006 | Grodzins et al. | |
| 7,174,001 B2 * | 2/2007 | Andrews et al. | 378/141 |
| 7,198,001 B1 | 4/2007 | Lewis et al. | |
| 7,209,539 B2 | 4/2007 | De Smet | |
| 7,400,701 B1 * | 7/2008 | Cason | 378/57 |
| 7,463,714 B2 | 12/2008 | Edwards et al. | |
| 7,476,023 B1 | 1/2009 | Canfield et al. | |
| 7,508,910 B2 | 3/2009 | Safai et al. | |
| 7,529,343 B2 | 5/2009 | Safai et al. | |
| 7,535,990 B2 | 5/2009 | Safai et al. | |
| 7,564,948 B2 * | 7/2009 | Wraight et al. | 378/101 |
| 7,567,649 B1 | 7/2009 | Safai et al. | |
| 7,623,626 B2 | 11/2009 | Safai et al. | |
| 7,649,967 B2 | 1/2010 | Jonsson et al. | |
| 7,649,976 B2 | 1/2010 | Georgeson et al. | |
| 7,839,969 B2 * | 11/2010 | Gallup et al. | 378/45 |
| 8,396,187 B2 | 3/2013 | Safai | |
| 8,503,610 B1 | 8/2013 | Safai | |
| 8,761,338 B2 * | 6/2014 | Safai | 378/86 |
| 2007/0206726 A1 | 9/2007 | Lu et al. | |
| 2009/0116614 A1 | 5/2009 | Kotowski et al. | |
| 2012/0321046 A1 | 12/2012 | Safai | |
| 2014/0064453 A1 | 3/2014 | Safai | |

OTHER PUBLICATIONS

"XRB701 Monoblock 200KV @ 400 Watts," Spellman High Voltage Electronics Corporation, pp. 1-3, Hauppage, New York, Retrieved on Jun. 7, 2011. http://www.spellmanhv.cn/~/media/Files/Products/XRB401.ashx.

"High Voltage Power Supply and X-Ray Generator Company," Spellman High Voltage Electronics Coporation, pp. 1-2, Retrieved on Jun. 7, 2011. http://www.spellmanhv.com.

Shedlock, et al., "X-Ray Backscatter Imaging for Aerospace Applications," 5 pages, retrieved on Nov. 23, 2010.

BMT Defense Services and Amtec Consultants, Ltd., "The Feasibility of a Corrosion Resistant Ship," 2008 (15 pages).

"Discussion of Methods for Underwater Bridge Inspection, Section 5: In-Depth Inspections," retrieved on Aug. 30, 2011 (9 pages) http://onlinemanuals.txdot.gov/txdotmanuals/ins/indepth_inspections.htm.

Schmitt, "Global Needs for Knowledge Dissemination, Research, and Development in Materials Deterioration and Corrosion Control," The World Corrosion Organization, May 2009 (44 pages).

American Science and Engineering, Inc., "Products and Solutions: Securing Ports, Border Crossings and High-Threat Facilities and Events," retrieved on Aug. 30, 2011. http://www.as-e.com/products_solutions/index.asp (2 pages).

Office Action, dated Apr. 26, 2013, regarding USPTO Application No. 13/164,583, 24 pages.

Towe et al., "X-Ray Backscatter Imaging", IEEE Transactions on Biomedical Engineering, vol. BME-28, No. 9, Sep. 1981, pp. 646-654.

Partial European Search Report, dated Apr. 12, 2013, regarding Application No. EP12172727.5, 8 pages.

"The Feasability of a Corrosion Resistant Ship", BMT Defense Services and Amtec Consultants, Inc., copyright 2006, 2008, 17 pages. Accessed Jul. 26, 2013, http://www.amteccorrosion.co.uk/corrosion%20resistant%20ship.html.

Shedlock et al., "X-Ray Backscatter Imaging for Aerospace Applications", AIP Conference Proceedings, vol. 1335, Jun. 2011, pp. 509-516.

Notice of Allowance, dated Feb. 14, 2014, regarding U.S. Appl. No. 13/164,583, 19 pages.

\* cited by examiner

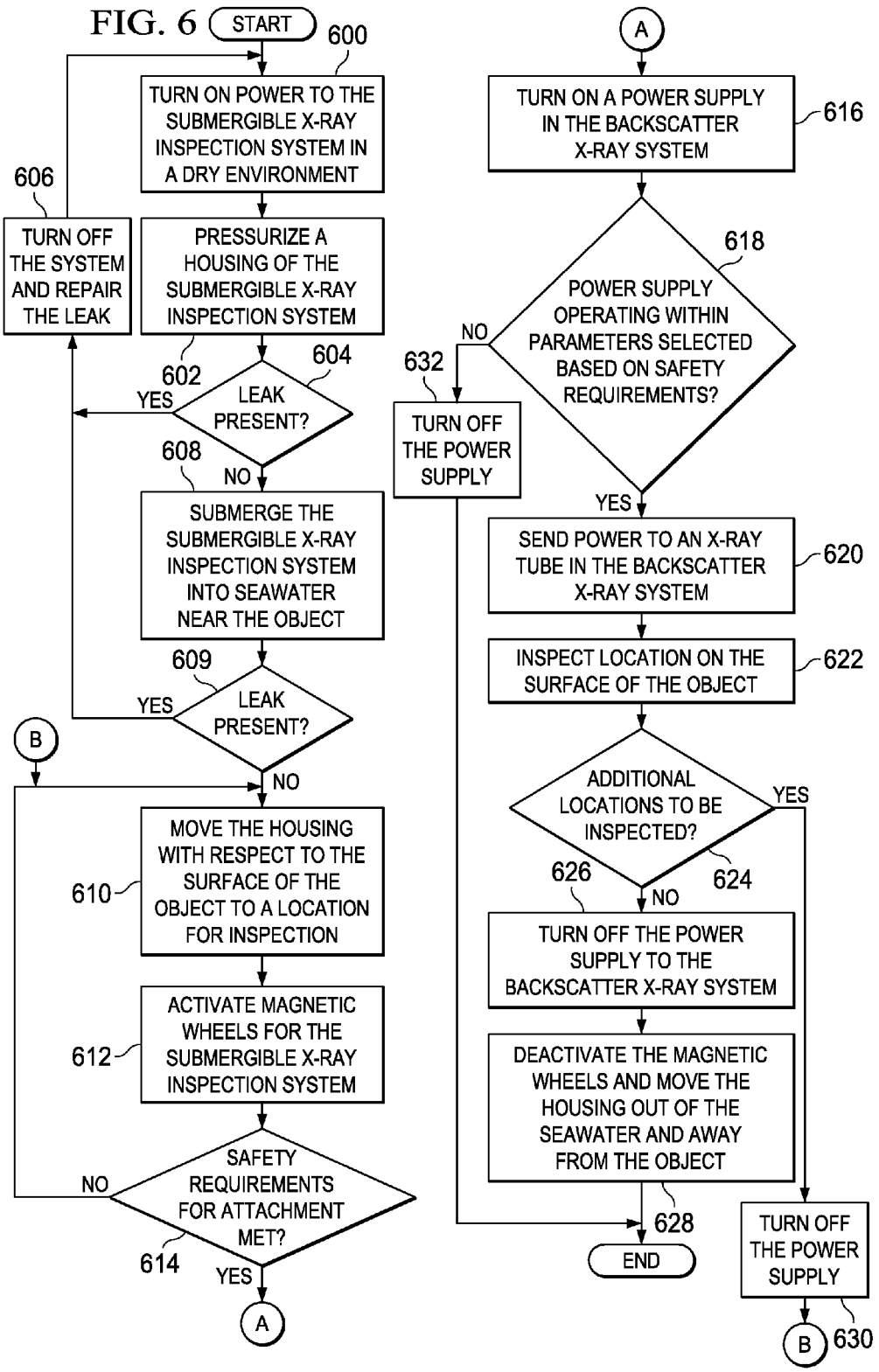

SYSTEM FOR INSPECTING OBJECTS UNDERWATER

CROSS-REFERENCE TO RELATED APPLICATION

This application is related to the following patent application entitled "Integrated Backscatter X-Ray System", Ser. No. 13/164,583, filed Jun. 20, 2011, assigned to the same assignee, and incorporated herein by reference.

BACKGROUND INFORMATION

1. Field

The present disclosure relates generally to x-ray systems and, in particular, to backscatter x-ray systems. Still more particularly, the present disclosure relates to a method and apparatus for inspecting objects underwater using a backscatter x-ray system.

2. Background

In some situations, visual inspection of a surface of an object may not provide the information needed to determine whether inconsistencies are present on the surface or subsurface of the object. In these situations, non-destructive inspection (NDI) systems may be used to test the object. Non-destructive inspection systems are inspection systems that are configured to test an object for inconsistencies without causing undesired effects to the object. Non-destructive inspection systems also may be referred to as non-destructive evaluation (NDE) systems, non-destructive examination (NDE) systems, and non-destructive testing (NDT) systems.

Different types of non-destructive inspection systems are currently available. These different types of non-destructive inspection systems include, but are not limited to, ultrasonic testing (UT) systems, eddy current testing systems, x-ray systems, backscatter x-ray systems, and other types of sensor systems configured to test an object without causing undesired effects to the object.

Non-destructive inspection systems may be used to test objects in different types of environments and in different types of conditions. For example, when the object to be inspected is an aircraft, a non-destructive inspection system may be used to test the aircraft while the aircraft is located in a hangar and/or when the aircraft is being operated. As another example, the object to be inspected may be a ship. A non-destructive inspection system may be used to test the ship while the ship is not operating and is located in dry dock.

However, depending on an environment in which an object is located, some currently available non-destructive inspection systems may be unable to perform an inspection of the object in the environment. Further, some currently available non-destructive inspection systems may be unable to provide information about inconsistencies on a surface or subsurface of an object with a desired level of accuracy when the object is located in a particular environment.

Accordingly, it would be advantageous to have a method and apparatus that takes into account one or more of the issues discussed above, as well as possibly other issues.

SUMMARY

In one advantageous embodiment, an apparatus comprises a housing, an x-ray system located inside of the housing, and a cooling system. The cooling system is associated with the housing and is configured to cool a number of components for the x-ray system using water from an environment around the housing.

In another advantageous embodiment, an apparatus comprises a housing, an x-ray system, and a movement system. The housing is configured to substantially prevent water in an environment around the housing from entering the housing through undesired locations. The x-ray system is located inside of the housing. The movement system is configured to move the housing and the x-ray system with respect to a surface of an object.

In yet another advantageous embodiment, a method for operating an inspection system is provided. A housing with an x-ray system located inside of the housing is moved in an environment with water relative to a location on a surface of an object to be inspected. The location on the surface of the object is submerged in the water in the environment. A number of components for the x-ray system are cooled using the water around the housing.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof will best be understood by reference to the following detailed description of an advantageous embodiment of the present disclosure when read in conjunction with the accompanying drawings, wherein:

FIG. 6 is an illustration of a process in the form of a flowchart for operating an inspection system to inspect an object in accordance with an advantageous embodiment.

DETAILED DESCRIPTION

The different advantageous embodiments recognize and take into account different considerations. For example, the different advantageous embodiments recognize and take into account that inconsistencies in an object may be present beneath an outermost layer of the surface of the object. For example, inconsistencies may be present beneath a coat of paint on the surface of an object. The different advantageous embodiments recognize and take into account that non-destructive inspection (NDI) systems may be used to evaluate these and other types of inconsistencies.

However, the different advantageous embodiments also recognize and take into account that some currently available non-destructive inspection systems may not provide information about the inconsistencies in an object with a desired level of accuracy when the object is at least partially submerged in water. As one illustrative example, some currently available non-destructive inspection systems may be unable to generate images of a portion of the surface of an object that provide desired information about inconsistencies in the object when the portion of the surface is submerged in water.

The different advantageous embodiments recognize and take into account that backscatter x-ray systems are configured to inspect large areas as compared to the areas that may be inspected using other types of non-destructive inspection systems. Further, the different advantageous embodiments recognize and take into account that backscatter x-ray systems may have the capability to generate substantially real-time images of a surface of an object for use in the identification of inconsistencies. However, the different advantageous embodiments recognize and take into account that currently available backscatter x-ray systems may not be configured for operation underwater.

Thus, the different advantageous embodiments provide an inspection system configured to operate underwater. In particular, the inspection system may be used to inspect an object that is at least partially submerged in water.

In one advantageous embodiment, an apparatus comprises a housing, an x-ray system located inside of the housing, a cooling system, and a movement system. The housing is configured to substantially prevent water in an environment around the housing from entering the housing through undesired locations. The cooling system is associated with the housing and is configured to cool a number of components for the x-ray system using water from an environment around the housing. The movement system is configured to move the housing and the x-ray system with respect to a surface of an object.

Figure 1:
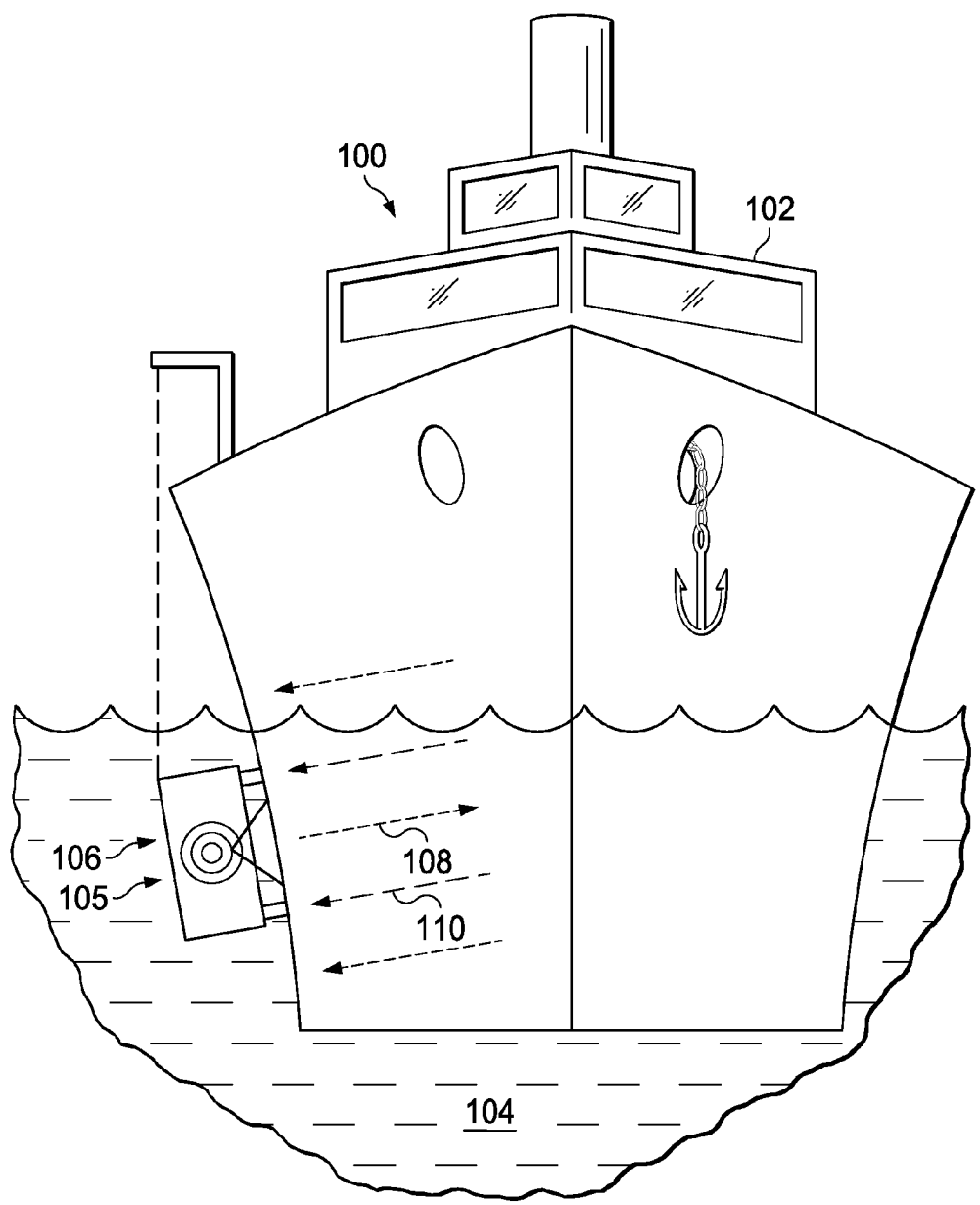
FIG. 1 is an illustration of an inspection environment in accordance with an advantageous embodiment.

With reference now to FIG. 1, an illustration of an inspection environment is depicted in accordance with an advantageous embodiment. In this illustrative example, inspection environment 100 includes ship 102 that is to be inspected. As depicted, a portion of ship 102 is underwater. More specifically, a portion of ship 102 is submerged in water 104.

In this illustrative example, inspection system 105 is configured to inspect ship 102 in inspection environment 100. Inspection system 105 takes the form of submergible x-ray inspection system 106. Submergible x-ray inspection system 106 is capable of being immersed in and/or remaining in water 104 without water 104 affecting the operation of submergible x-ray inspection system 106.

As depicted, submergible x-ray inspection system 106 is configured to operate underwater such that the portion of ship 102 that is submerged in water 104 may be inspected. In particular, submergible x-ray inspection system 106 generates x-rays 108 that are directed towards ship 102. A portion of x-rays 108 are reflected off of the surface of ship 102. The portion of x-rays 108 that are reflected off of the surface of ship 102 are referred to as backscatter 110.

Submergible x-ray inspection system 106 is configured to detect backscatter 110. Further, submergible x-ray inspection system 106 generates images using backscatter 110. These images may be used to identify inconsistencies in ship 102.

Figure 2:
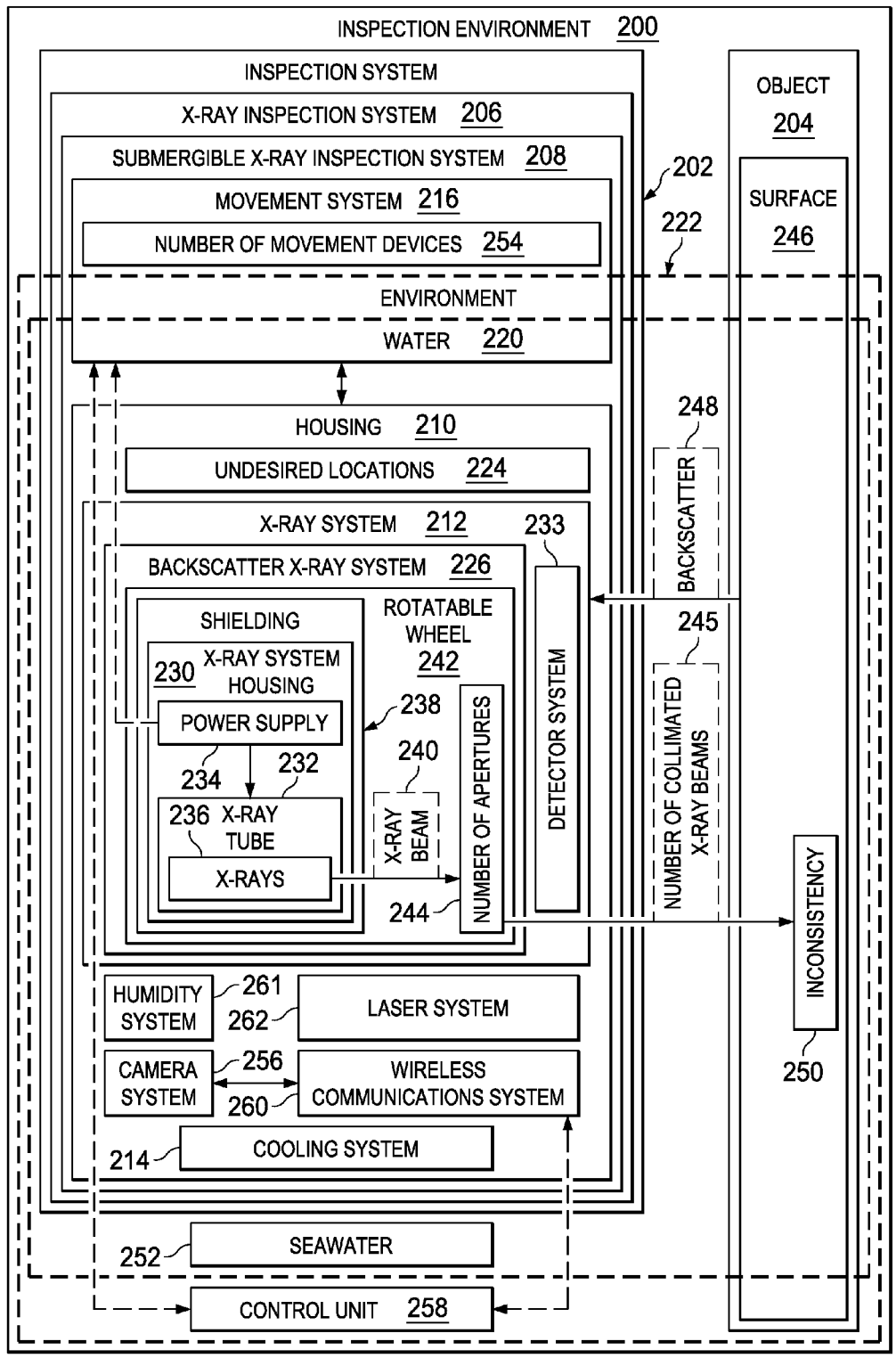
FIG. 2 is an illustration of an inspection environment in the form of a block diagram in accordance with an advantageous embodiment.

With reference now to FIG. 2, an illustration of an inspection environment in the form of a block diagram is depicted in accordance with an advantageous embodiment. Inspection environment 100 in FIG. 1 is an example of one implementation for inspection environment 200 in FIG. 2. In these illustrative examples, inspection environment 200 includes inspection system 202 and object 204 to be inspected using inspection system 202.

Object 204 may take a number of different forms in these illustrative examples. In particular, object 204 may be any object that is configured to operate in and/or underwater. Further, object 204 may be any object that may be at least partially submerged in water. As one illustrative example, object 204 may take the form of a ship, such as ship 102 in FIG. 1. In other illustrative examples, object 204 may be selected from one of a submarine, a water-based vehicle, an oil tanker, an oil rig, a pipe, an oil pipe, a gas pipe, a bridge, a bridge pylon, a port, a pier, an underwater structure, or some other suitable type of object.

In these illustrative examples, inspection system 202 takes the form of x-ray inspection system 206. More specifically, inspection system 202 may take the form of submergible x-ray inspection system 208. Submergible x-ray inspection system 106 in FIG. 1 is an example of one implementation for submergible x-ray inspection system 208.

Inspection system 202 includes housing 210, x-ray system 212, movement system 216, and cooling system 214. In these illustrative examples, housing 210 is a first housing for inspection system 202. Housing 210 is configured to substantially prevent water 220 that may be present in environment 222 around housing 210 from entering housing 210 through undesired locations 224 in housing 210. Undesired locations 224 may include any locations not selected for receiving water 220. In this manner, housing 210 may be substantially water-proof.

Environment 222 around housing 210 may take a number of different forms. For example, without limitation, environment 222 may be selected from one of an ocean, a sea, a river, a lake, a pond, a pool, a water tank, a water reservoir, or some suitable type of environment 222 containing water 220.

X-ray system 212, cooling system 214, and movement system 216 are associated with housing 210 in these depicted examples. When one component, such as movement system 216, is "associated" with another component, such as housing 210, the association is a physical association in these depicted examples.

For example, a first component, such as movement system 216, may be considered to be associated with a second component, such as housing 210, by being secured to the second component, bonded to the second component, mounted to the second component, welded to the second component, fastened to the second component, and/or connected to the second component in some other suitable manner. The first component also may be connected to the second component using a third component. The first component also may be considered to be associated with the second component by being formed as part of and/or an extension of the second component.

In these illustrative examples, x-ray system 212 is located inside of housing 210. Depending on the implementation, x-ray system 212 may take the form of backscatter x-ray system 226. In one illustrative example, backscatter x-ray system 226 includes x-ray system housing 230, x-ray tube 232, detector system 233, and power supply 234.

X-ray system housing 230 is a second housing for inspection system 202. X-ray system housing 230 is configured to house the components needed for generating x-rays 236. X-rays 236 are waves in the electromagnetic spectrum that have wavelengths from about 0.01 nanometers to about 10 nanometers. X-rays 236 form electromagnetic radiation referred to as x-radiation. X-ray system housing 230 may be formed from a number of materials that allow x-rays 236 to pass through x-ray system housing 230. As used herein, a "number of" items, when used with reference to items, means one or more items. For example, a number of materials means one or more materials.

In these illustrative examples, shielding 238 is provided around sections of x-ray system housing 230 at which x-rays 236 passing through x-ray system housing 230 are not desired. Shielding 238 is a material that substantially prevents x-rays 236 from passing through shielding 238. In these illustrative examples, shielding 238 absorbs x-rays 236 at locations on x-ray system housing 230 at which shielding 238 is present. In one illustrative example, shielding 238 may be composed at least partially of lead.

As depicted, x-ray tube 232 and power supply 234 are located inside of x-ray system housing 230. X-ray tube 232 may include, for example, without limitation, a vacuum tube, a cathode, and a rotatable anode. In these depicted examples, the cathode and the rotatable anode are located inside of the vacuum tube.

The cathode emits electrons. The vacuum tube is configured to accelerate the electrons emitted from the cathode such that the electrons collide with the rotatable anode. In particular, the rotatable anode is configured to generate x-rays 236 in response to receiving the electrons emitted by the cathode. The rotatable anode has metallic properties that cause x-rays 236 to be generated in response to the electrons colliding with the rotatable anode. For example, the rotatable anode may be made up at least partially of rhodium or tungsten.

X-rays 236 generated by the rotatable anode are generated in a particular direction towards a window in the vacuum tube. The portion of x-rays 236 that pass through the window and out of the vacuum tube form x-ray beam 240. The window may be composed of beryllium, glass, aluminum, or another suitable material that allows x-rays 236 to pass through the window.

In these illustrative examples, backscatter x-ray system 226 also includes rotatable wheel 242. X-ray system housing 230 is positioned within an interior of rotatable wheel 242. Rotatable wheel 242 has number of apertures 244. Each aperture is a hole or an opening in rotatable wheel 242.

Rotatable wheel 242 is configured to rotate while x-ray tube 232 generates x-rays 236. Rotatable wheel 242 may rotate about 360 degrees in these depicted examples. As rotatable wheel 242 rotates, number of apertures 244 in rotatable wheel 242 also rotates. A portion of x-ray beam 240 is allowed to pass through one or more of number of apertures 244 as rotatable wheel 242 rotates.

The portion of x-ray beam 240 that passes through an aperture in number of apertures 244 forms an x-ray beam that is collimated in a direction through the aperture. In these illustrative examples, collimating a portion of x-ray beam 240 means causing the rays of the portion of x-ray beam 240 to be substantially parallel in one direction. In some illustrative examples, collimating the portion of x-ray beam 240 also includes reducing the radius of the portion of x-ray beam 240.

In this manner, the portion of x-ray beam 240 that passes through the aperture is a collimated x-ray beam. Number of collimated x-ray beams 245 may be formed as rotatable wheel 242 rotates, while x-rays 236 are being generated. In these illustrative examples, each of number of collimated x-ray beams 245 is directed towards a particular location on surface 246 of object 204.

A portion of each of number of collimated x-ray beams 245 that encounters surface 246 is absorbed by object 204, while another portion is reflected off of surface 246. The portion that is reflected off of surface 246 is referred to as backscatter 248.

Detector system 233 in x-ray system 212 is configured to detect backscatter 248 that is formed in response to number of collimated x-ray beams 245 encountering surface 246 of object 204. In particular, backscatter 248 is formed by x-rays within number of collimated x-ray beams 245 reflecting off of surface 246 when the x-rays encounter surface 246.

Further, number of collimated x-ray beams 245 may encounter inconsistency 250 in object 204. In these illustrative examples, inconsistency 250 may be on surface 246 of object 204, under an outer layer of surface 246 of object 204, or within object 204. When number of collimated x-ray beams 245 encounters inconsistency 250 on surface 246, a portion of backscatter 248 may be formed in a direction that is not detected by detector system 233, while another portion of backscatter 248 may be formed in a direction that is detected by detector system 233. In this manner, backscatter 248 detected by detector system 233 may be used to identify inconsistency 250 and any other inconsistencies that may be present in object 204.

In these illustrative examples, detector system 233 may be associated with housing 210 and may be located outside of x-ray system housing 230. Detector system 233 may take a number of different forms and comprise any number of detectors. For example, detector system 233 may comprise any number of scintillator detectors, solid state detectors, and/or other suitable types of detectors.

In these illustrative examples, x-ray tube 232 is powered by power supply 234 in x-ray system housing 230. Further, power supply 234 may be used to power any number of other components in backscatter x-ray system 226. Depending on the implementation, power supply 234 may be configured to generate power within backscatter x-ray system 226. In this manner, backscatter x-ray system 226 may be configured to operate autonomously.

Integrating power supply 234 and x-ray tube 232 into x-ray system housing 230 reduces a need for providing shielding 238 for both power supply 234 and x-ray tube 232. When power supply 234 and x-ray tube 232 are integrated into x-ray system housing 230, backscatter x-ray system 226 may be referred to as an integrated backscatter x-ray system.

Further, with power supply 234 and x-ray tube 232 in x-ray system housing 230, cooling system 214 may be used to cool both power supply 234 and x-ray tube 232 in x-ray system housing 230. Cooling system 214 may be considered part of backscatter x-ray system 226 in some illustrative examples.

As depicted, cooling system 214 may be configured to receive water 220 from environment 222 around housing 210 of inspection system 202 and allow water 220 to enter x-ray system housing 230 to cool a number of components of backscatter x-ray system 226. For example, cooling system 214 may allow water 220 to enter x-ray system housing 230 to cool power supply 234 and x-ray tube 232 inside of x-ray system housing 230.

As one illustrative example, cooling system 214 may include a first channel configured to receive water 220 at an opening in housing 210 and allow water 220 to flow into x-ray system housing 230. Water 220 that flows into x-ray system housing 230 may cool a number of components for backscatter x-ray system 226 that are inside of x-ray system housing 230. Water 220 that flows into x-ray system housing 230 is heated by the components in backscatter x-ray system 226 inside of x-ray system housing 230 to form heated water.

Further, cooling system 214 may include a second channel configured to allow this heated water to flow out of x-ray system housing 230, out of housing 210 at another opening of housing 210, and into environment 222 around housing 210. Additionally, in these illustrative examples, undesired locations 224 in housing 210 through which water 220 is substantially prevented from entering housing 210 may be locations other than the openings in housing 210 for the first channel and the second channel.

The first channel and the second channel may be formed in a number of different ways. For example, the first channel and the second channel may be inside a first hose and a second hose, respectively. These hoses may have first ends at openings of housing 210 and second ends at openings of x-ray system housing 230. In other illustrative examples, the first channel and the second channel may be formed as part of housing 210. In still other illustrative examples, the first channel and the second channel may be formed by pipes, tubes, and/or other suitable structures.

In these illustrative examples, when environment 222 takes the form of the ocean or the sea, water 220 may be seawater 252. Seawater 252 in environment 222 may be used to cool the components of backscatter x-ray system 226 such that a different type of coolant is not needed. Using seawater 252 may reduce the cost and/or weight of backscatter x-ray system 226 as compared to using a coolant, such as oil.

Further, movement system 216 is configured to move housing 210 and x-ray system 212 inside of housing 210 with respect to surface 246 of object 204. For example, movement system 216 may move housing 210 and x-ray system 212 with respect to surface 246 of object 204 to move x-ray system 212 to a location on surface 246 of object 204 to be inspected.

Movement system 216 may include any number of structures and/or devices configured to move housing 210. As one illustrative example, movement system 216 includes number of movement devices 254. Number of movement devices 254 may include at least one of, for example, without limitation, a wheel, a track, a roller, a slider, a crane, a robotic arm, a suction cup, and other suitable types of movement devices.

As used herein, the phrase "at least one of", when used with a list of items, means different combinations of one or more of the listed items may be used and only one of each item in the list may be needed. For example, "at least one of item A, item B, and item C" may include, for example, without limitation, item A, or item A and item B. This example also may include item A, item B, and item C, or item B and item C. In other examples, "at least one of" may be, for example, without limitation, two of item A, one of item B, and ten of item C; four of item B and seven of item C; and other suitable combinations.

In some illustrative examples, number of movement devices 254 may be connected to a structure in movement system 216 that is connected to housing 210. The structure may be, for example, a frame, a scaffolding system, or some other suitable type of structure. As one illustrative example, number of movement devices 254 may include four magnetic wheels attached to a structure connected to housing 210. These magnetic wheels may be configured to magnetically attach to surface 246 of object 204 when surface 246 is a metallic surface.

In these illustrative examples, movement system 216 may receive power from power supply 234. However, in other illustrative examples, movement system 216 may receive power from a different power supply associated with housing 210. In one illustrative example, movement system 216 may receive power from a source in a location remote to housing 210 of inspection system 202.

In some illustrative examples, inspection system 202 may include camera system 256. Camera system 256 may be located inside of housing 210 of inspection system 202. Camera system 256 may include, for example, a processor unit and a number of cameras. Camera system 256 may be configured to generate images for surface 246 of object 204 reflecting backscatter 248 and/or generate images of an area in environment 222 around inspection system 202.

As one illustrative example, images of the area around inspection system 202 may take the form of, for example, photographs, video, infrared images, and/or other suitable types of images. These images may be used to control movement of housing 210. For example, these images may be used to identify uneven portions of surface 246 and/or identify obstacles in a path of submergible x-ray inspection system 208.

For example, these images may be stored in camera system 256. Further, these images may be transmitted wirelessly to control unit 258 using wireless communications system 260 in inspection system 202. Wireless communications system 260 may be associated with housing 210 and/or x-ray system housing 230 and may be configured to allow wireless communications between control unit 258 and inspection system 202.

For example, control unit 258 may be in a location remote to inspection system 202. Control unit 258 may be used to control operation of inspection system 202. In particular, control unit 258 may be used to control operation of one or more of x-ray system 212, movement system 216, power supply 234 in x-ray system 212, camera system 256, and/or other components in inspection system 202.

As one illustrative example, an operator may enter user input at control unit 258. Control unit 258 may be used to control operation of x-ray system 212, movement system 216, power supply 234 in x-ray system 212, camera system 256, and/or other components in inspection system 202 based on this user input. In this manner, inspection system 202 may be remotely operated by an operator.

The illustration of inspection environment 200 in FIG. 2 is not meant to imply physical or architectural limitations to the manner in which an advantageous embodiment may be implemented. Other components in addition to and/or in place of the ones illustrated may be used. Some components may be unnecessary. Also, the blocks are presented to illustrate some functional components. One or more of these blocks may be combined, divided, or combined and divided into different blocks when implemented in an advantageous embodiment.

In some illustrative examples, power supply 234 may be located outside of x-ray system housing 230 but inside of housing 210. Cooling system 214 may use water 220 from environment 222 to cool power supply 234 inside of housing 210 and use a second coolant to cool x-ray tube 232 inside of x-ray system housing 230.

In other illustrative examples, additional components may be present in housing 210 and/or x-ray system housing 230. For example, a computer system may be located inside of housing 210 in some illustrative examples. The computer system may be used to control operation of x-ray system 212.

In other illustrative examples, laser system 262 may be present inside housing 210. Laser system 262 may project a laser beam onto surface 246 of object 204. The laser beam may be projected at the location at which number of collimated x-ray beams 245 is encountering object 204. In another advantageous embodiment, the laser beam may be projected at a location at which number of collimated x-ray beams 245 will encounter object 204 at a future point in time.

Additionally, in some illustrative examples, humidity system 261 also may be present inside housing 210. Humidity system 261 may be configured to monitor humidity levels within housing 210. When humidity levels within housing 210 are not within selected tolerances, humidity system 261 may be configured to initiate safety operations. These safety operations may include, for example, shutting down the supply of power to submergible x-ray inspection system 208, generating an alert, and/or performing other suitable types of safety operations.

Figure 3:
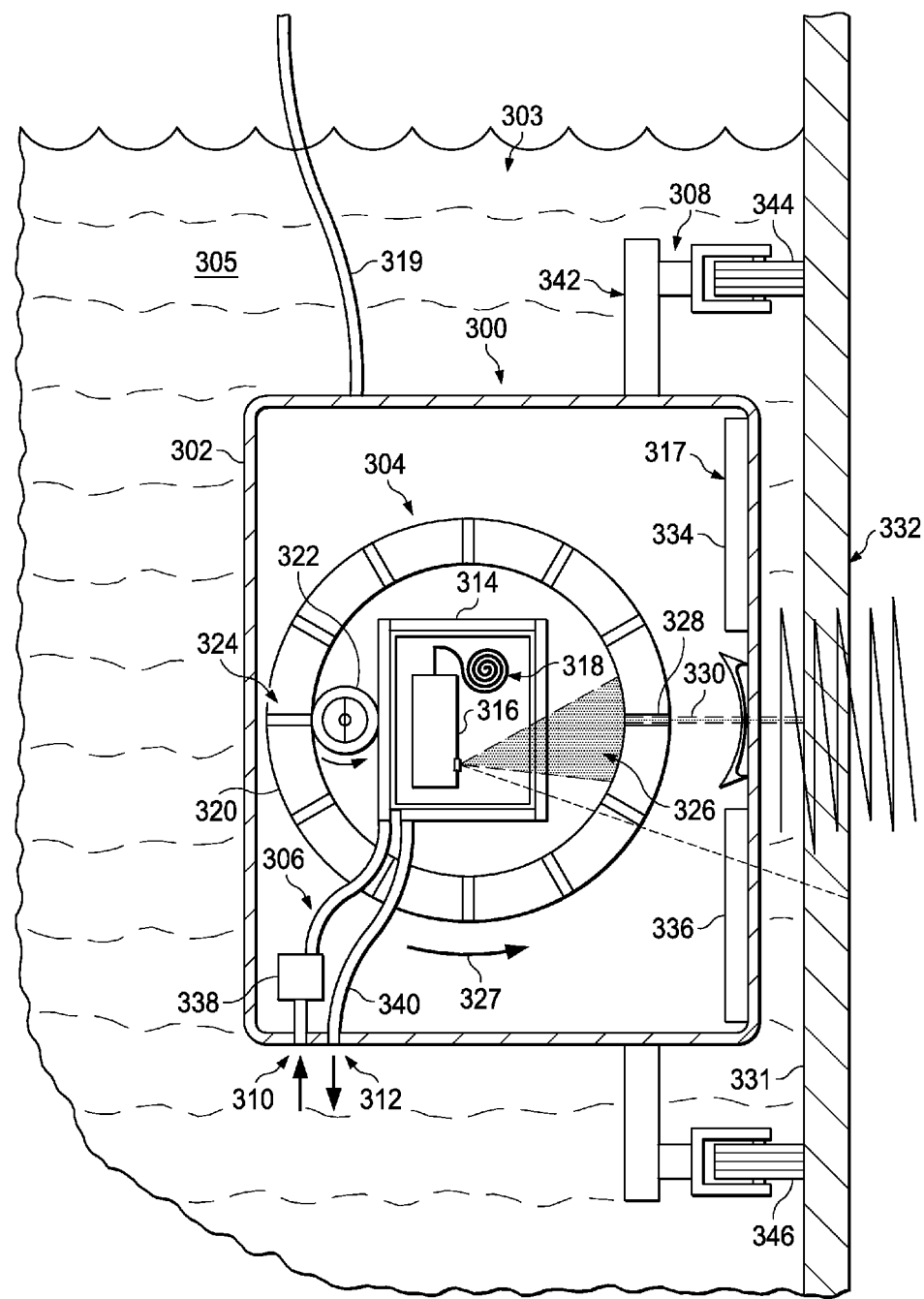
FIG. 3 is an illustration of a submergible x-ray inspection system performing inspection of a submarine in accordance with an advantageous embodiment.

With reference now to FIG. 3, an illustration of a submergible x-ray inspection system performing inspection of a submarine is depicted in accordance with an advantageous embodiment. In these illustrative examples, submergible x-ray inspection system 300 is an example of one implementation for submergible x-ray inspection system 208 in FIG. 2. Submergible x-ray inspection system 300 is submerged in seawater 305 in sea 303 in this illustrative example.

As depicted, submergible x-ray inspection system 300 includes housing 302, backscatter x-ray system 304, cooling system 306, and movement system 308. Housing 302 is an example of one implementation for housing 210 in FIG. 2. In this illustrative example, housing 302 is configured to substantially prevent seawater 305 around housing 302 from entering housing 302 through locations other than opening 310 and opening 312. In this manner, locations on housing 302 other than opening 310 and opening 312 are examples of undesired locations 224 in FIG. 2.

Backscatter x-ray system 304 is located inside of housing 302. Backscatter x-ray system 304 is an example of one implementation for backscatter x-ray system 226 in FIG. 2. As depicted, backscatter x-ray system 304 includes housing 314, x-ray tube 316, detector system 317, power supply 318, rotatable wheel 320, and motor 322. X-ray tube 316 and power supply 318 are located inside of housing 314. Detector system 317 is located outside of housing 314 and is associated with housing 302.

In this illustrative example, power supply 318 may be configured to provide power to one or more of x-ray tube 316, detector system 317, and motor 322. Power supply 318 is configured to receive power through power cable 319. Power cable 319 may be connected to a power source, such as, for example, a generator, an outlet, or some other suitable type of power source.

In this illustrative example, x-ray tube 316 is configured to generate x-ray beam 326. Motor 322 is configured to rotate rotatable wheel 320 while x-ray beam 326 is being generated. In particular, motor 322 may rotate rotatable wheel 320 in the direction of arrow 327. As rotatable wheel 320 rotates, a portion of x-ray beam 326 passes through number of apertures 324 in rotatable wheel 320. As one illustrative example, a portion of x-ray beam 326 may pass through aperture 328 in number of apertures 324 in rotatable wheel 320. The portion of x-ray beam 326 that passes through aperture 328 forms collimated x-ray beam 330.

Collimated x-ray beam 330 is formed such that collimated x-ray beam 330 encounters surface 331 of submarine 332. In this illustrative example, surface 331 may be the surface of a side of submarine 332.

Detector system 317 is configured to detect backscatter (not shown) formed in response to a portion of collimated x-ray beam 330 that encounters surface 331 being reflected off of surface 331. As depicted, detector system 317 includes detector 334 and detector 336.

In this illustrative example, cooling system 306 includes first hose 338 and second hose 340. First hose 338 is configured to receive seawater 305 through opening 310 in housing 302 and allow seawater 305 to flow into housing 314. Seawater 305 that flows into housing 314 is used to cool the components inside housing 314. In particular, this water may be used to cool power supply 318 and x-ray tube 316.

The water that is inside of housing 314 is heated by power supply 318 and x-ray tube 316 to form heated water. Second hose 340 is configured to allow this heated water to flow out of housing 314 and out of housing 302 through opening 312 of housing 302.

In this illustrative example, movement system 308 is configured to move housing 302 and backscatter x-ray system 304 located inside of housing 302 with respect to surface 331 of submarine 332. In particular, movement system 308 includes structure 342, magnetic wheel 344, and magnetic wheel 346.

Structure 342 is connected to housing 302. Structure 342 may be configured to move housing 302. Further, structure 342 is connected to magnetic wheel 344 and to magnetic wheel 346. Magnetic wheel 344 and magnetic wheel 346 are configured to attach to surface 331 of submarine 332 once structure 342 has moved housing 302 to a desired location. Further, magnetic wheel 344 and magnetic wheel 346 may move over surface 331 to allow housing 302 to be moved to different locations with respect to surface 331 of submarine 332.

Figure 4:
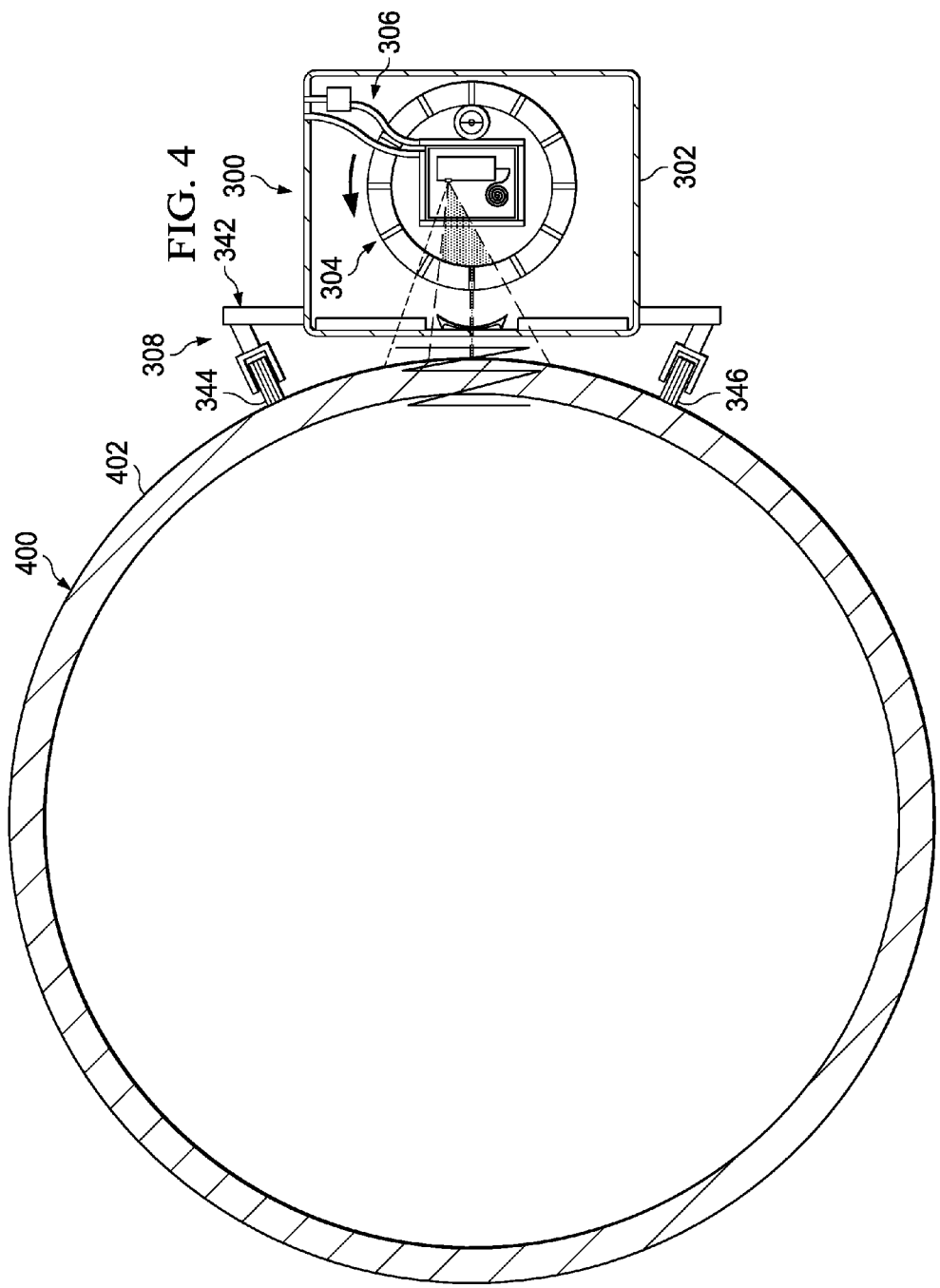
FIG. 4 is an illustration of a submergible x-ray inspection system performing inspection of an oil pipe in accordance with an advantageous embodiment.

Turning now to FIG. 4, an illustration of a submergible x-ray inspection system performing inspection of an oil pipe is depicted in accordance with an advantageous embodiment. In this illustrative example, submergible x-ray inspection system 300 from FIG. 3 is performing an inspection of oil pipe 400. As depicted, magnetic wheel 344 and magnetic wheel 346 of movement system 308 attach to surface 402 of oil pipe 400 such that housing 302 with backscatter x-ray system 304 located inside of housing 302 may be moved with respect to surface 402 of oil pipe 400.

Figure 5:
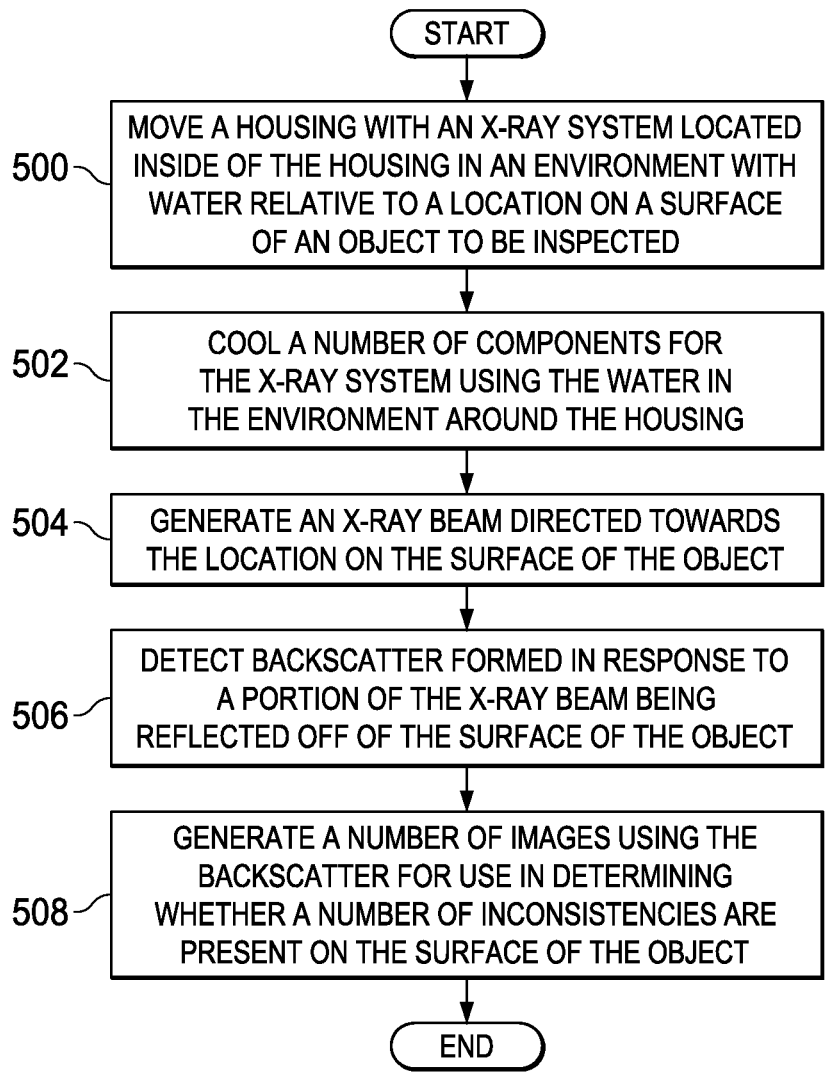
FIG. 5 is an illustration of a process in the form of a flowchart for operating an inspection system in accordance with an advantageous embodiment.

With reference now to FIG. 5, an illustration of a process in the form of a flowchart for operating an inspection system is depicted in accordance with an advantageous embodiment. The process illustrated in FIG. 5 may be implemented using inspection system 202 in FIG. 2.

The process begins by moving a housing with an x-ray system located inside of the housing in an environment with water relative to a location on a surface of an object to be inspected (operation 500). In operation 500, the location on the surface of the object is submerged in the water in the environment.

The process then cools a number of components for the x-ray system using the water in the environment around the housing (operation 502). In operation 502, the components cooled may include, for example, an x-ray tube, a power supply, and/or other suitable components for the x-ray system.

Thereafter, the process generates an x-ray beam directed towards the location on the surface of the object to be inspected (operation 504). The process then detects backscatter formed in response to a portion of the x-ray beam being reflected off of the surface of the object (operation 506). Next, the process generates a number of images using the backscatter for use in determining whether a number of inconsistencies are present on the surface of the object (operation 508), with the process terminating thereafter.

With reference now to FIG. 6, an illustration of a process in the form of a flowchart for operating an inspection system to inspect an object is depicted in accordance with an advantageous embodiment. The process illustrated in FIG. 6 may be implemented using submergible x-ray inspection system 106 in FIG. 1, submergible x-ray inspection system 208 in FIG. 2, submergible x-ray inspection system 300 in FIG. 3, and/or some other suitable type of submergible x-ray inspection system. This submergible x-ray inspection system may be used to inspect an object, such as, for example, without limitation, a submarine or some other object configured to operate in water.

The process begins by turning on power to the submergible x-ray inspection system in a dry environment (operation 600). In operation 600, the dry environment may be, for example, on land or on a portion of the surface of the object not submerged in water. In this illustrative example, the submergible x-ray inspection system comprises a housing, a backscatter x-ray system inside of the housing, a cooling system, and a movement system.

The process then pressurizes a housing of the submergible x-ray inspection system (operation 602). The process determines whether a leak is present in the housing (operation 604). In operation 604, determining whether a leak is present may include checking safety interlocks and/or other safety mechanisms associated with the housing to ensure that the housing is substantially water proof.

If a leak is present in the housing, the process turns off the system and repairs are made to stop the leak (operation 606). The process then returns to operation 600 as described above.

With reference again to operation 604, if a leak is not present in the housing, the process submerges the submergible x-ray inspection system into seawater near the object (operation 608). The process then again determines whether a leak is present (operation 609). If a leak is present, the process returns to operation 606 as described above.

Otherwise, the process moves the housing with respect to the surface of the object to a location for inspection (operation 610). In operation 610, a robotic structure connected to the housing may be configured to move the housing.

Thereafter, the process activates magnetic wheels for the submergible x-ray inspection system to magnetically attach the submergible x-ray inspection system to the surface of the object (operation 612). The magnetic wheels may be attached to the robotic structure in this illustrative example.

A determination is made as to whether safety requirements for the attachment of the magnetic wheels to the surface of the object have been met (operation 614). In operation 614, this determination may be made based on whether safety mechanisms associated with the magnetic wheels for attachment of the magnetic wheels to the surface of the object are operating within selected parameters. If the safety requirements for the attachment have been met, the process turns on a power supply in the backscatter x-ray system (operation 616).

The process then determines whether the power supply is operating within parameters selected based on safety requirements (operation 618). This determination may be made based on a number of factors. For example, this determination may be based on whether the power being generated by the power supply is within a desired range of power.

If the power supply is operating within the parameters selected, the process sends power from the power supply to an x-ray tube in the backscatter x-ray system (operation 620). The process then inspects the location on the surface of the object (operation 622).

The process determines whether additional locations on the surface of the object are to be inspected (operation 624). If additional locations are not to be inspected, the process turns off the power supply to the backscatter x-ray system (operation 626). The process then deactivates the magnetic wheels and moves the housing out of the seawater and away from the object (operation 628), with the process terminating thereafter.

With reference again to operation 624, if additional locations are to be inspected, the process turns off the power supply (operation 630). The process then returns to operation 610 as described above.

Further, with reference again to operation 618, if the power supply is not operating within the parameters selected, the process turns off the power supply (operation 632), with the process terminating thereafter. With reference again to operation 614, if the safety requirements for the attachment have not been met, the process returns to operation 610 as described above.

The flowcharts and block diagrams in the different depicted embodiments illustrate the architecture, functionality, and operation of some possible implementations of apparatuses and methods in an advantageous embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an advantageous embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, operation 609 in FIG. 6 may be repeated continuously while the submergible x-ray inspection system is submerged in the seawater. In this manner, a leak that may begin during operation of the submergible x-ray inspection system may be identified and repaired when the leak occurs.

Thus, the different advantageous embodiments provide an inspection system configured to operate underwater. In particular, the inspection system may be used to inspect an object that is at least partially submerged in water.

In one advantageous embodiment, an apparatus comprises a housing, an x-ray system located inside of the housing, a cooling system, and a movement system. The housing is configured to substantially prevent water in an environment around the housing from entering the housing through undesired locations. The cooling system is associated with the housing and is configured to cool a number of components for the x-ray system using water from an environment around the housing. The movement system is configured to move the housing and the x-ray system with respect to a surface of an object.

The description of the different advantageous embodiments has been presented for purposes of illustration and description and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:
1. An apparatus comprising:
a first housing;
an x-ray system located inside of the first housing, the x-ray system comprising a number of components comprising: a second housing located inside of the first housing, a power supply located inside of the second housing, and an x-ray tube located inside of the second housing; and a cooling system associated with the first housing and configured to cool the number of components using water from an environment around the first housing.

2. The apparatus of claim 1, wherein the first housing is configured to substantially prevent the water in the environment from entering the first housing through undesired locations.

3. The apparatus of claim 1, wherein the cooling system comprises:

a first channel configured to allow the water from the environment around the first housing to flow into the second housing to cool the power supply and the x-ray tube, wherein the water inside of the second housing is heated by the power supply and the x-ray tube to form heated water; and a second channel configured to allow the heated water to flow out of the second housing into the environment around the housing.

4. The apparatus of claim 1, wherein the x-ray system further comprises:

a rotatable wheel having a number of apertures, wherein the rotatable wheel is associated with the second housing and is configured to rotate while the x-ray tube generates an x-ray beam such that the number of apertures allows at least a portion of the x-ray beam to pass through the rotatable wheel; and a detector configured to detect a backscatter in response to the at least the portion of the x-ray beam encountering an object.

5. The apparatus of claim 1, wherein the environment is selected from one of an ocean, a sea, a river, a lake, a pond, a pool, a water tank, and a water reservoir.

6. The apparatus of claim 1, wherein the water is seawater.

7. The apparatus of claim 1, further comprising:

a wireless communications system associated with the first housing, the wireless communications system configured to allow wireless communications between: the x-ray system, and a control unit located in an inspection environment.

8. The apparatus of claim 7, further comprising:

a camera system in communication with the wireless communications system.

9. The apparatus of claim 1, further comprising:

a movement system connected to the first housing and configured to move the first housing and the x-ray system with respect to a surface of an object.

10. The apparatus of claim 9, wherein the movement system comprises:

a number of movement devices configured to move the first housing and the x-ray system with respect to the surface of the object.

11. The apparatus of claim 10, wherein the number of movement devices includes at least one of a magnetic movement device, a wheel, a track, a roller, a slider, a crane, a robotic arm, and a suction cup.

12. The apparatus of claim 11, wherein the object is selected from one of a submarine, a ship, a pipe, an oil pipe, a gas pipe, a bridge, an underwater structure, and a water-based vehicle.

13. An apparatus comprising:

a housing configured to substantially prevent water in an environment around the housing from entering the housing through undesired locations;

an x-ray system, comprising a number of components, located inside of the housing;

a cooling system configured to cool the number of components for the x-ray system using the water in the environment; and a movement system configured to move the housing and the x-ray system with respect to a surface of an object.

14. A method for operating an inspection system, the method comprising:

moving a housing with an x-ray system located inside of the housing in an environment with water relative to a location on a surface of an object to be inspected, wherein the location on the surface of the object is submerged in the water in the environment; and cooling, using the water around the housing, a number of components comprised by the x-ray system.

15. The method of claim 14, further comprising:

generating an x-ray beam directed towards the location on the surface of the object; and detecting backscatter formed in response to a portion of the x-ray beam being reflected off of the surface of the object.

16. The method of claim 15, further comprising:

generating a number of images using the backscatter for use in determining whether a number of inconsistencies is present in the object.

17. The method claim 14, wherein the housing is a first housing and the x-ray system comprises a second housing, an x-ray tube located inside of the second housing, and a power supply located inside of the second housing and wherein cooling the number of components for the x-ray system using the water around the housing comprises:

allowing the water around the housing to enter the housing through a first channel and flow into the second housing to cool the x-ray tube and the power supply located inside of the second housing, wherein the water inside of the second housing is heated by the power supply and the x-ray tube to form heated water; and allowing the heated water to flow out of the second housing through a second channel to the environment around the housing.

18. The method of claim 14, wherein the housing is configured to substantially prevent the water in the environment from entering the housing through undesired locations.

\* \* \* \* \*